(12) United States Patent
Gueret (10) Patent No.: US 7,597,495 B2
(45) Date of Patent: Oct. 6, 2009

(54) DEVICE FOR APPLYING A SUBSTANCE

(75) Inventor: Jean-Louis H. Gueret, Paris (FR)

(73) Assignee: L'Oréal S.A., Paris (FR)

( * ) Notice: Subject to any disclaimer, the term of this patent is extended or adjusted under 35 U.S.C. 154(b) by 496 days.

(21) Appl. No.: 11/147,432

(22) Filed: Jun. 8, 2005

(65) Prior Publication Data

US 2005/0286966 A1 Dec. 29, 2005

Related U.S. Application Data

(60) Provisional application No. 60/580,359, filed on Jun. 18, 2004.

(30) Foreign Application Priority Data

Jun. 8, 2004 (FR) .................................. 04 51133

(51) Int. Cl.
*B05C 21/00* (2006.01)
(52) U.S. Cl. ..................... 401/130; 401/196
(58) Field of Classification Search ................ 401/202, 401/196, 130, 123–126
See application file for complete search history.

(56) References Cited

U.S. PATENT DOCUMENTS

| | | | | |
|---|---|---|---|---|
| 3,107,672 A | * | 10/1963 | Hofmann | .................... 607/151 |
| 3,221,359 A | * | 12/1965 | Moroni et al. | .............. 401/130 |
| 4,752,147 A | * | 6/1988 | Persi | .......................... 401/123 |
| 5,090,402 A | | 2/1992 | Bazin et al. | |
| 5,395,175 A | * | 3/1995 | Bontoux et al. | ................ 401/1 |
| 5,970,581 A | * | 10/1999 | Chadwick et al. | .............. 401/6 |
| 6,341,400 B1 | | 1/2002 | Kobayashi et al. | |
| 6,385,487 B1 | * | 5/2002 | Henley | ......................... 604/20 |
| 2003/0129016 A1 | | 7/2003 | Gueret | |

FOREIGN PATENT DOCUMENTS

| | | |
|---|---|---|
| EP | 1 086 904 A1 | 3/2001 |
| FR | 2 196 575 | 3/1974 |
| JP | 49-68891 | 6/1974 |
| JP | 63-174653 | 7/1988 |
| JP | 08 266328 | 10/1996 |
| JP | 2001-151285 | 6/2001 |
| JP | 2004 236722 | 8/2004 |
| WO | WO99/62372 | 12/1999 |

OTHER PUBLICATIONS

French Search Report for FR 04 51133, dated Feb. 11, 2005.
English language abstract of EP 1 086 904 A1, Mar. 28, 2001.
English language abstract of JP 08 266328, Oct. 15, 1996.
English language abstract of JP 2004 236722, Aug. 26, 2004.

* cited by examiner

*Primary Examiner*—David J Walczak
(74) *Attorney, Agent, or Firm*—Finnegan, Henderson, Farabow, Garrett & Dunner, L.L.P.

(57) ABSTRACT

A device for applying a substance, in some examples, may include an applicator element including a surface and being configured to be loaded with a substance, and an electrical exciter including at least two electrodes permanently in contact with the applicator element and enabling electric current to flow to the applicator element via the electrodes.

46 Claims, 3 Drawing Sheets

DEVICE FOR APPLYING A SUBSTANCE

This application claims the benefit under 35 U.S.C. § 119 (e) of U.S. Provisional Application No. 60/580,359, filed on Jun. 18, 2004.

The present invention relates to devices for applying a substance. In particular, various exemplary embodiments of the present invention relate to applicator devices for applying cosmetic products, including care products.

The term "cosmetic product," as used throughout the description, including the claims, has a meaning that encompasses (but is not necessarily limited to) the definition of a cosmetic product in the Jun. 14, 1993 Directive 93/35/EEC amending the Directive 76/768/EEC.

U.S. Patent Application Publication No. US 2003/0129016 discloses an applicator device for applying a substance. The device comprises a receptacle containing the substance to be applied and a porous structure defining an application surface for applying the substance. The porous structure may be fed with the substance.

There exists a need for further improving such applicator devices. In particular, there exists a need for facilitating or reinforcing the performance of the substance on the treated region of the body (e.g., the face) and/or for creating novel application effects.

Although the present invention may obviate one or more of the above-mentioned needs, it should be understood that some aspects and embodiments of the invention might not necessarily obviate one or more of those needs.

In the following description, certain aspects and embodiments will become evident. It should be understood that the invention, in its broadest sense, could be practiced without having one or more features of these aspects and embodiments. It should also be understood that these aspects and embodiments are merely exemplary.

In one aspect, as embodied and broadly described herein, the invention may provide a device for applying a substance. The device may comprise an applicator element comprising a surface, wherein the applicator may be configured to be loaded with the substance (e.g., the applicator element and/or its surface may be suitable for filling with the substance), and an electrical exciter comprising at least two electrodes permanently in contact with the applicator element and enabling electrical current to flow to the applicator element via the electrodes.

As used herein, the term "permanently in contact" is intended to designate a condition in which the electrodes are maintained in contact with the applicator element at least so long as the device is in an operating state. Where appropriate, however, it does not exclude the possibility that the applicator element may be separable from the electrodes, in particular in order to be replaced by another applicator element, between uses of the device.

According to at least some embodiments, the invention may provide numerous optional advantages. For example, the applicator element may be reloaded (e.g., refilled) with substance in relatively simple manner, e.g., by putting a surface of said applicator element into contact with the substance. In addition, the applicator device may be configured to be handled in relatively easy manner.

Moreover, the flow of electricity through the electrodes may contribute, for example, to opening and dilating the pores of the skin, thereby facilitating the action and/or the penetration of at least one active agent of the substance into the skin.

Where appropriate, the device may also make it possible to activate microcirculation of the blood to, for example, improve muscle tone or the healing capacity of the skin.

According to another aspect of the invention, the applicator element may be electrically conductive when dry. Thus, electric current may flow through the applicator element (via the electrodes) independently of whether the substance for application is itself electrically conductive or not. Where appropriate, this arrangement may enable the applicator element to be heated locally.

In still another aspect, the applicator element may comprise a material that is intrinsically generally non-conductive, such as, for example, a plastic material. In an aspect, the material may contain a filler that is electrically conductive.

In some exemplary aspects, the filler may comprise electrically conductive particles. For example, the filler may comprise at least one of metal particles and graphite particles. The metal particles may comprise at least one of copper, aluminum, and silver.

Alternatively or additionally, the applicator element may comprise magnetic particles (e.g., coated magnetic particles) in order to create a magnetic field. In use, the effects of the magnetic field may add to the advantageous effects of the applied electric current.

In another aspect of the invention, the applicator element may be electrically insulative when dry. In this case, electric current flow may be established through the applicator element (via the electrodes) only when the applicator element is impregnated with an electrically conductive substance.

Alternatively, in order to increase the magnitude of the electric current flowing to the applicator element via the electrodes, the applicator element may be electrically conductive when dry, and the substance may also be electrically conductive.

According to another aspect of the invention, the applicator element may be porous and/or elastically deformable. In some exemplary aspects, the applicator element may comprise at least one of a foam, a sintered element, a felt, a tuft of bristles, and a piece of elastomer.

In an aspect, the applicator element may comprise a material that is adapted to retain the substance by capillarity. For example, the applicator element may comprise a tuft of bristles or a flexible part made of, for example, silicone or elastomer and adapted to retain the substance by capillarity.

In some aspects, the applicator element may have a multi-layer structure. For example, the applicator element may have at least one conductive layer sandwiched between two other layers. By way of example only, the applicator element may comprise, in succession going from the outside towards the inside: an outer layer of felt; a conductive layer, such as, for example, metallic layer (e.g., made of aluminum); and a layer of foam; and at least one of the electrodes optionally being connected to the conductive layer.

In an exemplary aspect, the applicator element may be hydrophilic.

According to another aspect of the invention, at least one of the electrodes, and in particular a terminal portion thereof, may be at least partially embedded in the applicator element. The at least partially embedded electrode may avoid any direct contact with the skin. In some examples, such a characteristic may be advantageous, especially when the electrode is made of metal.

In some aspects, at least one of the electrodes may lack any contact with a surface of the applicator element that may be configured to contact a zone to which the substance is to be applied.

In one aspect, the electrodes may match the outside shape of the applicator element and present a surface that is rounded or flat, for example.

In another aspect, at least one of the electrodes may come flush with the outside surface of the applicator element. For example, the electrode may comprise, for example, a rounded head to avoid any injury to the user.

According to still another aspect of the invention, the device may comprise a handle, wherein at least one of the electrodes may be fixedly secured to the handle.

In another aspect, the device may comprise a compartment for receiving an electrical power supply, enabling the electrodes to be powered electrically. For example, according to still another aspect of the invention, the electrical power supply may comprise at least one of a capacitor and at least one optionally-rechargeable battery.

While in use, according to one aspect, the voltage across terminals of the electrodes may be identical to the voltage across the terminals of the electrical power supply.

In a variant, the electrical exciter may comprise a connector for connecting the electrical exciter to an electrical adapter. The electrical adapter may be connected to mains (i.e., an electrical utility (e.g., via an electrical power outlet such as a common female wall outlet that receives a male plug)).

According to some aspects, a voltage across the terminals of the electrodes may be less than about 30 volts (V). For example, the voltage across the terminals of the electrodes may range from about 1 V to about 9 V.

According to still another aspect, the electrical exciter may comprise an indicator light configured to indicate whether electrical current is flowing through the electrodes. For example, the indicator light may be configured to light up when electrical current is flowing through the electrodes. In some exemplary embodiments, the light may comprise one or more light-emitting diodes (LED), possibly of different colors.

In one aspect, the electrical exciter may comprise a power adjuster member for adjusting electrical power supplied to the electrodes (e.g., for adjusting the maximum current and/or voltage, in particular a potentiometer or a contactor having a plurality of positions).

In another aspect, the electrical exciter may comprise a switch, such as, for example, a pushbutton, for controlling the supply of electrical power to the electrodes, and in particular for enabling the device to be switched on and off.

According to one aspect of the invention, the applicator device may comprise a reservoir containing the substance. The reservoir may be arranged to feed (e.g., reload and/or refill) the applicator element with the substance.

In some aspects, the substance present in the reservoir may be electrically conductive. For example, the substance may contain mineral salts.

In another aspect of the invention, the substance may be a skin care product and/or a cosmetic product. For example, the substance may comprise a hair care product. In some exemplary embodiments, the substance may be suitable for forming a film over the zone to be treated.

In one aspects, the device may comprise a receptacle comprising a supply of substance and an applicator comprising a handle secured to the applicator element. The applicator may be configured to be removably placed on the receptacle so as to enable loading the applicator element with the substance.

In another aspect, the applicator may comprise a compartment for accommodating an electrical power supply. For example, in some exemplary embodiments, the handle may comprise said compartment for accommodating the electrical power supply.

According to still another aspect of the invention, the receptacle may comprise a housing for receiving the applicator element when the applicator is removably placed on the receptacle. For example, the housing may comprise an end wall arranged to restrict the passage of the substance from the reservoir to the applicator element. In some exemplary embodiments, said end wall may comprise one or more orifices.

According to an aspect, when the applicator element is received in the housing of the receptacle for storage purposes, the applicator element may optionally be compressed.

In another aspect of the invention, the device may comprise a receptacle containing the substance to be applied, wherein the applicator element may be permanently fastened on the receptacle. In still another aspect, the receptacle may comprise a compartment for accommodating an electrical power supply.

According to yet still another aspect, the device may comprise a case, that is distinct from the receptacle, configured to accommodate an electrical power supply and to releasably receive at least part of said receptacle. The case may comprise first electrical contacts arranged to co-operate with second electrical contacts secured to the receptacle for supplying electrical current to the electrodes.

In another aspect of the invention, the device may comprise a handle with a compartment for accommodating an electrical power supply. The compartment may be provided with a resilient return member (e.g., one disposed at the end of the compartment) arranged to urge the electrical power supply away from a first position, in which the electrical power supply may connect to the electrodes, towards a second position, in which the electrical power supply may be disconnected from the electrodes. In order to supply electricity to the electrodes, the user may exert a force on the electrical power supply against a return force exerted by the resilient return member, so as to bring the electrical power supply into the first position. The device thus need not have a switch that may be separate from the electrical power supply, thereby simplifying its structure.

In still another aspect, the resilient return member may comprise a spring, such as, for example, a helical spring.

In one aspect, the receptacle may comprise a housing for fixedly or removably receiving the application element. The housing may be in fluid communication with a reservoir of substance.

Another aspect of the invention may provide an applicator comprising a handle, an applicator element secured to the handle and comprising a surface, the applicator element being configured to be loaded with substance, and an electrical exciter comprising at least two electrodes permanently in contact with the applicator element and enabling electrical current to flow to the applicator element via the electrodes.

In some aspects of the invention, the applicator may lack any reservoir of substance associated with the applicator element for feeding the applicator element with substance.

In another aspect, the applicator may comprise a compartment for accommodating an electrical power supply.

Some aspects of the invention may provide a method of performing cosmetic treatment (e.g., for treating a zone of the skin). The method may comprise providing any of the devices described herein; loading (e.g., filling) the applicator element with a substance; and applying the substance to a zone to be treated via the applicator element.

In another aspect, the method may further comprise causing electrical current to flow through the electrodes while simultaneously applying the substance to the zone for treatment.

Where appropriate, the electrical current may be applied sequentially, either manually (e.g. by operating a switch of the device) or automatically (e.g., by using a suitable electronic circuit).

In some aspects, the substance may be applied using the applicator element without causing electrical current to flow through the electrodes. For example, according to another aspect, the method may comprise causing electric current to flow through the electrodes substantially without applying any additional quantity of substance. The applicator element may be in contact with the zone that has already been covered with the substance.

In one aspect, for an applicator element that may be electrically insulating when dry, the method may comprise loading the applicator element with a substance that is electrically conductive, and causing electrical current to flow through the electrodes.

In another aspect, the invention may provide a device for applying a substance. The device may comprise a handle, an applicator element comprising a surface, the applicator element being secured to the handle at least while the substance is being applied, the applicator element (e.g., at least its surface) being configured to be loaded (e.g., filled) with the substance, and an electrical exciter comprising at least two electrodes in contact with the applicator element and enabling electrical current to flow through the electrodes.

In still another aspect, the invention may provide a device for applying a substance, the device comprising an applicator element comprising a surface, the applicator element (e.g., its surface) being configured to be loaded (e.g., filled) with the substance, an electrical exciter comprising at least two electrodes in contact with the applicator element and enabling electricity to flow through the electrodes (e.g. when desired), and a handle with a compartment for housing an electrical power supply for electrically powering the electrical exciter. The compartment may be provided with a resilient return member arranged to move the electrical power supply from a first position, in which the electrical power supply may power the electrodes, towards a second position, in which the electrical power supply may be disconnected from the electrodes.

In yet still another aspect, the invention may provide a device for applying a substance, the device comprising an applicator element comprising a surface and being configured to be loaded with substance, the applicator element comprising at least one of: a foam, a sintered element, a felt, a piece of elastomer (e.g., silicone), and a tuft of bristles, and an electrical exciter comprising at least two electrodes in contact with the applicator element and enabling electrical current to flow through said electrodes.

Aside from the structural and procedural arrangements set forth above, the invention could include a number of other arrangements, such as those explained hereinafter. It is to be understood that both the foregoing description and the following description are exemplary.

The accompanying drawings, which are incorporated in and constitute a part of this specification, illustrate a number of non-limiting embodiments of the invention and together with the description, serve to explain the principles of the invention.

Reference will now be made in detail to the exemplary embodiments of the invention, examples of which are illustrated in the accompanying drawings. Wherever possible, the same reference numbers will be used throughout the drawings to refer to the same or like parts. It is to be understood that both the foregoing general description and the following detailed description are exemplary and explanatory only and are not restrictive of the invention, as claimed.

Figure 1:
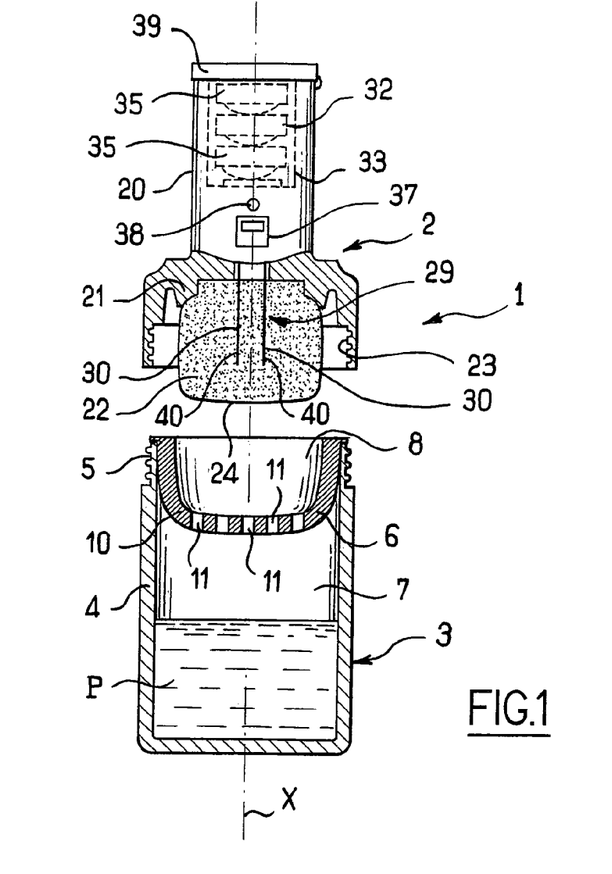
FIG. 1 is a diagrammatic, axial cross-sectional view of an applicator device, according to an exemplary embodiment of the invention.

FIG. 1 shows an applicator device 1 for applying a substance, according to an exemplary embodiment of the invention. The device 1 may comprise an applicator 2 and a receptacle 3. The receptacle 3 may be separated from the applicator 2. The receptacle 3 may comprise a body 4 having an axis X and defining a reservoir 7 for containing a substance P.

In the exemplary embodiments described, the substance P may be a cosmetic or skin care product for applying to skin. In a variant, the substance P may be a hair care product. By way of example only, the substance P may be a liquid or a powder.

The substance P may comprise at least one cosmetic or dermatological active agent. For example, the substance P may comprise at least one compound selected from the following materials: metals and alloys thereof, cobalt, barium, chromium, aluminum, silver, copper, titanium, bronze, manganese, metal oxides, iron oxides (e.g., ferrite), rare earths, silicates, sulfates (e.g., barium sulfate), carbonates (e.g., calcium carbonate), non-ferrous compounds (e.g., sulfur), magnesium, calcium, boron, potassium, carbon, oligo-elements, sea salt, rock salt, clay, steatite, algae and plankton and extracts therefrom, roots, licorice, ginger, oily waxes, proteins, hormones, collagens, alums (e.g., alumstone), glucose, vitamins (e.g., vitamin C, vitamin A, vitamin F, vitamin B, and vitamin E), plant extracts, glycerin, laponite, wetting agents, collagen, acids (e.g., salicylic acid and tio acid), caffeine, aromatic essential oils, coloring agents, antioxidizants, free radical scavengers, water absorbers, moisturizers, depigmenting agents, liporegulators, anti-acne agents, antidandruff agents, anti-aging agents, softeners, antiwrinkle agents, keratolitic agents, anti-inflammatory agents, fresheners, healing agents, vascular protectors, antibacterial agents, antifungal agents, antiperspirants, deodorants, skin conditioners, anesthetics, immunomodulators, and nourishing agents.

The body 4 of the receptacle 3 may comprise a neck 5 having an engagement portion (e.g., an outside thread) configured to engage with the corresponding engagement portion (e.g., an inner thread) of the applicator 2. Alternatively or additionally, the applicator 2 and the receptacle 3 may be engaged by snap-fastening, friction-fitting, and/or bayonet-type locking mechanism.

The receptacle 3 may also include a flow reducer 6 fixedly or removably disposed in the neck 5. The flow reducer 6 may form a housing 8. The housing 8 may be defined by an end wall 10 made in the form of a grid having a plurality of orifices 11. In a variant, the end wall 10 may have only one orifice.

The applicator 2 may comprise a handle 20 having a longitudinal axis X. In some exemplary embodiments, the longitudinal axis X of the handle 20 may coincide with the axis X of the receptacle 3. In the exemplary embodiment shown in FIG. 1, the handle 20 may be connected to a support portion 21 to which an applicator element 22 may be secured. The support portion 21 may comprise a threaded skirt 23 configured to engage the neck 5 of the receptacle 3 to close the device 1.

In some exemplary embodiments, the handle 20, the support portion 21, and the threaded skirt 23 may be molded as a single piece of, for example, plastic material.

The applicator element 22 may be secured to the support portion 21 in many different ways, such as, for example, by heat-sealing or adhesive, or with at least one fastener insert. Any other securing mechanism known in the art may additionally or alternatively be used.

The applicator element 22 may comprise an outside surface 24 that may be suitable for loading (e.g., filling) with substance P. At least a portion of the outside surface 24 may also be used to apply the substance P onto a zone to be treated. In the exemplary embodiment shown in FIG. 1, the applicator element 22 may comprise a foam. In an alternatively embodiment, the applicator element 22 may comprise a felt or a sintered element.

When the applicator 2 is placed on the receptacle 3, the applicator element 22 may be received in the housing 8. The applicator element 22 may be compressible such that, when the applicator 2 is received in the housing 8, the applicator element 22 may be compressed. In a variant, the housing 8 may be sufficiently large, so that the applicator element 22 may be received in the housing 8 without being compressed, regardless of whether the applicator element 22 is compressible or not.

The applicator 2 may comprise an electrical exciter 29 provided with a pair of electrodes 30. In some exemplary embodiments, the electrical exciter 29 may comprise more than two electrodes 30. The electrodes 30 may be electrically connected to an electrical power supply 32. In the exemplary embodiment shown in FIG. 1, the handle 20 may comprise a compartment 33 for accommodating the electrical power supply 32. By way of example only, these electrodes 30 may be fastened rigidly to the handle 20.

The electrical power supply 32 may comprise a plurality of button cells 35 connected in series, for example. In a variant, the electrical power supply may comprise a dry cell battery delivering 4.5 V or 9 V, for example. Of course, the invention is not limited to a particular type of electrical power supply 32. For example, the electrical power supply 32 may be a rechargeable battery, suitable for delivering electrical power of predefined magnitude, or a mains adapter (not shown).

The voltage delivered by the electrodes 30 may be a direct current (DC) voltage. In some alternative exemplary embodiments, however, the electrical exciter 29 may comprise an electronic circuit serving, for example, to deliver electrical power in the form of pulses or in the form of alternating current (AC) at a voltage that may be lower or higher than that delivered by the electrical power supply.

The electrical exciter 29 may comprise a switch 37 that may be disposed on an outside face of the applicator 2, enabling the electrical power supplied to the electrodes 30 to be controlled.

The electrical exciter 29 may also comprise an indicator light 38 configured to light up when a voltage is applied to the electrodes 30. In a variant, the indicator light 38 may be configured to light up when electrical current of predefined magnitude is flowing through the electrodes 30. In another variant, the indicator light 38 may shine, for example, with a first color when the electrodes 30 have a voltage applied thereto, and may shine with a second color when electric current flows through the two electrodes 30. Under such circumstances, the indicator light may comprise a two-color LED.

The handle 20 may comprise a closure cap 39 for closing the compartment 33. The closure cap 39 may be opened to, for example, replace the electrical power supply 32.

In the exemplary embodiment shown in FIG. 1, the electrodes 30 may be substantially cylindrical, each having a terminal portion 40. The terminal portion 40 may be fully embedded in the applicator element 22, even when the applicator element 22 is itself compressed. The electrodes 40 may be permanently embedded in, or in contact with, the applicator element 22. In some exemplary embodiments, the electrodes 40 may be removably arranged in the applicator element 22.

It should be understood that the electrodes 30 may have various forms. For example, the electrodes 30 may be flexible or stiff. The electrodes 30 may also be made of metal or any other material known in the art. Where appropriate, the electrodes 30 may also present a variety of shapes. For example, the electrodes 30 may be curved so as to facilitate holding of the applicator element 22 onto the support portion 21. In an exemplary embodiment, the electrodes 30 may be concentric.

The electrodes 30 may be fastened to the remainder of the device by any suitable means, such as, for example, crimping, heat-sealing, snap-fastening, or overmolding.

In an exemplary embodiment, the support portion 21 may be made of a conductive material (e.g., metal) and may constitute one of the electrodes.

The applicator element 22 may be electrically insulative when dry (e.g., being made of an electrically insulating material), and the substance P may be electrically conductive (e.g., containing mineral salts).

In accordance with an exemplary embodiment of the invention, the applicator device 1 of FIG. 1 may be used as follows. For convenience, it is assumed that, prior to a first use, the applicator 2 is placed on the receptacle 3 and the applicator element 22 is received in the housing 8. Prior to the first use, the applicator element 22 may be loaded (e.g., filled) with substance P by, for example, turning the device 1 upside-down (i.e., head down) or shaking the device 1, so that the substance P may flow from reservoir 7 through the orifices 11 towards the applicator element 22.

Alternatively or additionally, the receptacle body 4 may be elastically deformable, so that a user may squeeze the receptacle body 4 to reduce the volume of the reservoir 7, thereby causing the substance P to be expelled from the reservoir 7 through the orifices 11. In some exemplary embodiments, the receptacle 3 may comprise a dispensing pump (not shown) that may be configured to, upon actuation, dispense the substance P towards the applicator element 22.

Once the applicator element 22 has been loaded with the substance P, the applicator 2 may be separated from the receptacle 3, and the user may bring the applicator element 22 into contact with a surface or zone for treatment, such as, for example, the skin or hair. The substance P may then be deposited in the form of, for example, a film.

While applying the substance P to the treatment zone, the user may simultaneously supply electrical power to the electrodes 30 by, for example, actuating the switch 37. Since the applicator element 22 is loaded (e.g., filled) with the substance P that may be electrically conductive, electrical current may flow between the two electrodes 30 and over the region of the body (e.g., skin) that may be in contact with the applicator element 22.

The electrical current passing over the region of the body may, for example, activate microcirculation of the blood in the region, which may facilitate penetration of at least one of the active agents contained in the substance P into the skin.

In an alternative exemplary embodiment, the user may use the applicator 2 merely for applying the substance P to the treatment zone, without supplying any flow of electrical current.

In another exemplary embodiment, the user may initially apply the substance P to the treatment zone without generating a flow of electrical current and, once the substance P has been applied onto the treatment zone, the user may then supply electrical current over the treatment zone. While supplying the electrical current, the user may massage the treated zone without further applying the substance P thereto.

Of course, the user may also alternate the treatments with and without the application of electricity.

The electrical current may also be applied periodically by, for example, manipulating the switch 37 to cause electrical current to pass intermittently.

In some of the exemplary embodiments described above, the electrical exciter 29 has a switch that may be distinct from the electrical power supply 32. As described further herein, an electrical power supply may also comprise a switch.

Figure 2:
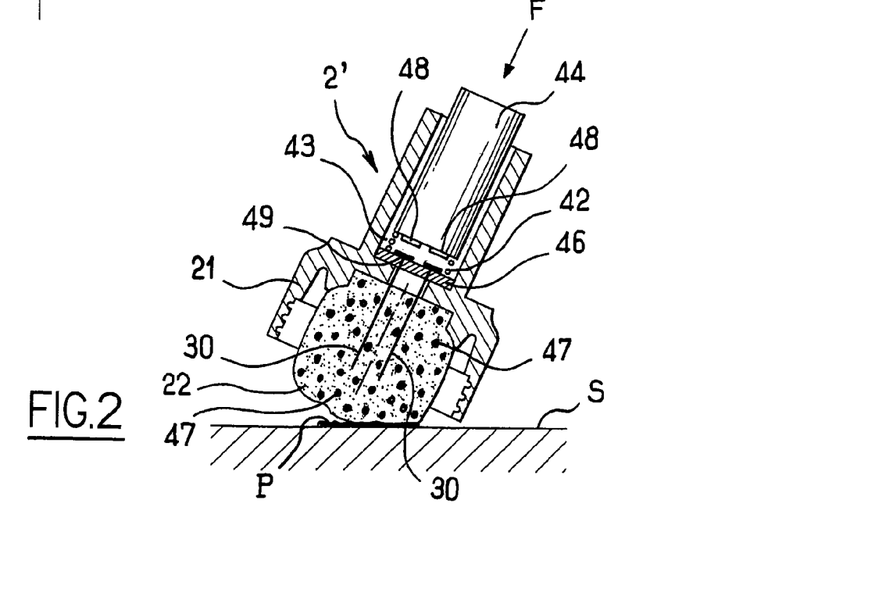
FIG. 2 is a diagrammatic, axial cross-sectional view of an applicator, according to another exemplary embodiment of the invention.

FIG. 2 shows an applicator 2' that differs from the applicator 2 of FIG. 1 in that it may include a resilient return member (e.g., a helical spring 42) disposed in a compartment 43 (e.g., near its bottom wall) that may be open at its top end. An electrical power supply 44 (e.g., a 9-volt dry battery) may be placed in the compartment 43. Pressing the power supply 44 against the resilient return member 42 in the compartment 43 may cause the power supply 44 to move between a first position in which the electrical power supply 44 may power the electrodes 30 and a second position in which the electrical power supply 44 may be disconnected from the electrodes 30.

In the first position, the two electrical terminals 48 of the electrical power supply 44 may come into contact with corresponding electrical terminals 49 disposed in the compartment 43 (e.g., on its end wall). By way of example only, the terminals 49 of the compartment 43 may be carried by an insert having the electrodes 30 fastened thereto.

While the substance P is being applied to the skin S, the user may exert sufficient force F on the electrical power supply 44 so as to bring it into the first position, which may allow electrical current to flow through the electrodes 30. On releasing the electrical power supply 44, the resilient return member 42 may move the electrical power supply 44 back into the second position, by which the supply of electrical power may be interrupted.

The applicator element 22 may be electrically conductive when dry. For example, as shown in FIG. 2, some exemplary embodiments of the applicator element 22 may comprise a substantially non-conductive material (e.g., a plastic material) containing an electrically conductive filler. Thus, the substance P may be generally non-conductive.

In various exemplary embodiments, the conductive filler may comprise electrically conductive particles 47, such as, for example, metal particles (e.g., particles of copper, silver, or aluminium) or graphite particles.

Alternatively or additionally, the applicator element 22 may comprise magnetic particles to combine the effects of both an electrical current and of a magnetic field.

In some exemplary embodiments, the applicator element 22 may be electrically insulative when dry. In these exemplary embodiments, the substance P may be electrically conductive.

According to another exemplary aspect of the invention, the applicator element may be permanently or releasably fastened to the receptacle.

Figure 3:
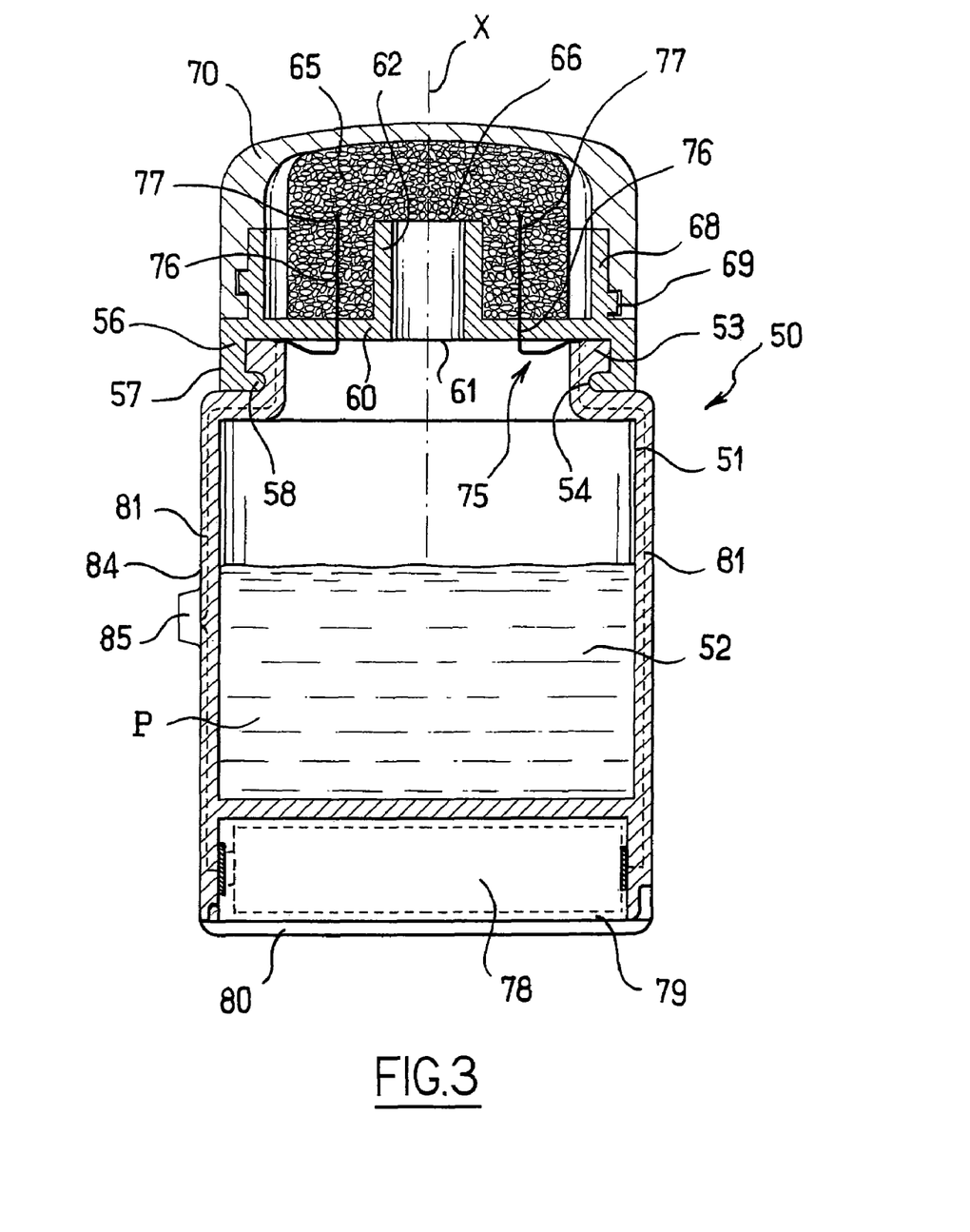
FIG. 3 is a diagrammatic, axial cross-sectional view of an applicator device, according to another exemplary embodiment of the invention.

By way of example only, FIG. 3 shows an applicator device 50 comprising a receptacle 51 defining a reservoir 52 for containing a substance P. The substance P may be in the form of, for example, a liquid or a powder.

The receptacle 51 may have a neck 53 having an axis X. The neck 53 may have an annular groove 54 for fastening a support 56 thereto. The bottom portion of the support 56 may comprise an assembly skirt 57 with an annular bead 58 suitable for snap-fastening with the groove 54 of the receptacle 51. The support 56 may also have a transverse wall 60 that may bear against the neck 53 of the receptacle 51. This transverse wall 60 may have a central orifice 61 opening out into a chimney 62.

The chimney 62 may have an elongation axis X, which may or may not be coincident with the axis X of the neck 53. This chimney 62 may be extended from the top surface of the wall 60. The chimney 62 may have a variety of cross-sectional shapes. For example, the chimney 62 may have a circular or elliptical shape.

The applicator element 65 may be made of a foam material, which may be suitable for loading (e.g., filling) with substance P.

The applicator element 65 may be permanently fastened to the support 56 by, for example, heat-sealing or adhesive-bonding. Any other fastening mechanism known in the art may also be used to fasten the applicator element 65 to the support 56.

In an alternative embodiment, the applicator element 65 may be releasably mounted to the support 56. This may enable the applicator element 65, where appropriate, to be replaced with another applicator element, which may have different size, shape, and/or surface appearance, for example. Thus, the user may select the appropriate type of applicator element depending on, for example, the substance P to be applied and/or the zone to be treated.

As shown in FIG. 3, the applicator element 65 may include a recess 66 for engaging with the chimney 62. The substance P may thus flow from the reservoir 52 of the receptacle 51 towards the applicator element 65 via the chimney 62. The receptacle 51 may have walls that may be elastically deformable so as to enable the user to squeeze the receptacle 51 to reduce its reservoir volume, causing the substance P to be expelled out through the chimney 62.

The support 56 may further comprise a cylindrical wall 68 extending along the axis X above the transverse wall 60. The wall 68 may comprise a thread 69 enabling a closure cap 70 to be screwed thereon.

Placing the closure cap 70 on the support 56 may cause the applicator element 65 to be compressed. In a variant, the applicator element 65 and the closure cap 70 may be arranged such that, when the closure cap 70 is placed on the support 56, the applicator element 65 may not be compressed.

The device 50 may include an electrical exciter 75 comprising two electrodes 76. The two electrodes 76 may be carried by the transverse wall 60 of the support 56. In the exemplary embodiment shown in FIG. 3, each of these electrodes 76 may include a terminal portion 77 that may be completely embedded in the applicator element 65.

The electrodes 76 may be fed with electrical power supplied from an electrical power supply 78 (e.g., a 1.5-volt battery shown by dashed lines in FIG. 3). This electrical power supply 78 may be accommodated in a compartment 79 formed in the bottom portion of the receptacle 51. This compartment 79 may be closed by a closure cap 80 that may be hinged onto the receptacle 51.

The electrical power supply 78 may be electrically connected to the electrodes 76 by electric wires 81. In an exemplary embodiment, the receptacle 51 may form one or more grooves in which the electric wires 81 may be received.

The electrical exciter 75 may comprise a switch 85 disposed on, for example, a side wall 84 of the receptacle 51 to control the supply of electricity to the electrodes 76.

The applicator element 65 may be electrically insulative when dry, and the substance P may be electrically conductive.

To use the applicator device 50, a user may load (e.g., fill) the applicator element 65 with substance P by, for example, placing the receptacle 51 upside-down (i.e., with its head pointing downwards), shaking the device 50, or, if the receptacle 51 is made of elastically deformable walls, squeezing the receptacle 51.

Once the applicator element 65 is loaded with substance P, the user may bring it into contact with the zone to be treated (e.g., the skin) and apply the substance P thereto.

Before, during, or after application of the substance P, the user may actuate the switch 85 to cause electrical current to flow through the electrodes 76. For example, the user may apply the substance P to the zone without causing any electrical current to flow through the electrodes 76.

The applicator element 65 may contain electrically conductive particles that may increase the magnitude of the electrical current flowing between the electrodes 76 and/or to facilitate passing of electrical current to the treatment zone.

Figure 4:
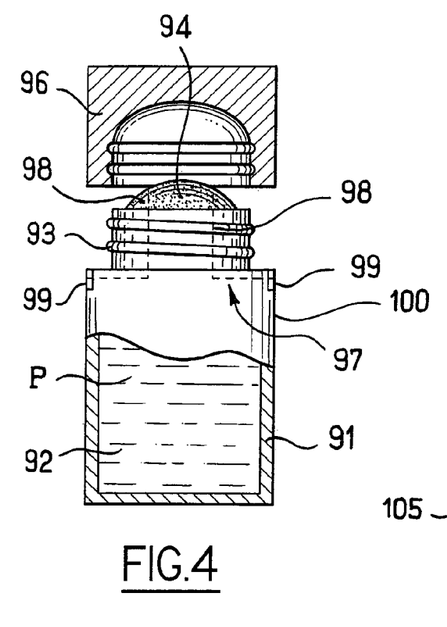
FIG. 4 is a diagrammatic, axial cross-sectional view of a receptacle for an applicator device, according to another exemplary embodiment of the invention.
Figure 5:
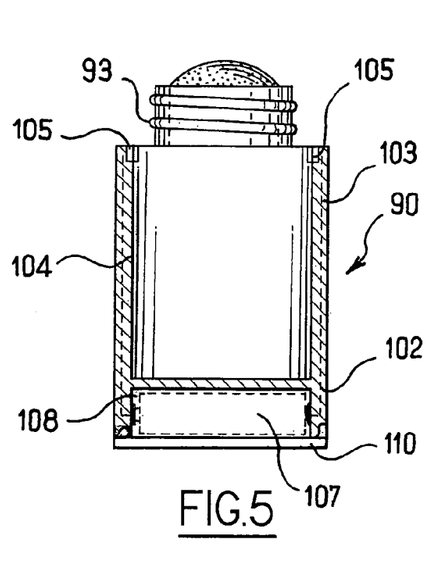
FIG. 5 is a diagrammatic, axial cross-sectional view of the applicator device shown in FIG. 4, showing the device placed in a case carrying an electrical power supply.

FIGS. 4 and 5 show an applicator device 90, according to still another exemplary embodiment of the invention. The device 90 may comprise a receptacle 91 defining a reservoir 92 for containing a substance P. The substance P may be substantially conductive, for example. The receptacle 91 may have a threaded neck 93 with an applicator element 94 housed therein. The threaded neck 93 may also allow a closure cap 96 to be screwed thereon.

The receptacle 91 may include an electrical exciter 97 provided with two electrodes 98 that may be at least partially embedded in the applicator element 94.

These electrodes 98 may be connected to electrical contacts 99 disposed on, for example, an outside surface 100 of the receptacle 91. The electrical contacts 99 may be close to the neck 93.

According to another exemplary embodiments, the applicator device 90 may further comprise a case 102 having a cylindrical wall 103 defining a housing 104 for receiving the receptacle 91, as shown in FIG. 5. The cylindrical wall 103, on its inside surface, may comprise electrical contacts 105 configured to be brought into contact with the corresponding contacts 99 of the receptacle 91 when the receptacle 91 is received in the housing 104.

The contacts 105 may be connected, via electric wires, for example, to an electrical power supply 107. The electrical power supply 107, as shown in FIG. 5, may be accommodated in a compartment 108 formed in the bottom portion of the case 102. The case 102 may have a closure cap 110 for closing the compartment 108.

The applicator device 90 shown in FIGS. 4 and 5 may be used as follows. If a user desires merely to apply substance P to the treatment zone, without generating any flow of electrical current, the receptacle 91 may be used separately from the case 102, as shown in FIG. 4.

If, however, a user desires to supply flow of electrical current to the treatment zone while applying the substance P, the user may place the receptacle 91 in the housing 104 of the case 102, so that the contacts 99 of the receptacle 91 and the contacts 105 of the case 102 may be electrically interconnected to enable electrical current to flow through the electrodes 98.

Figure 6:
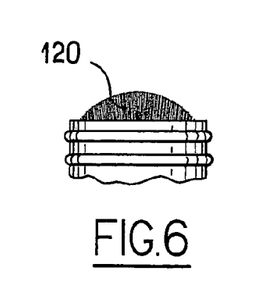
FIGS. 6 and 7 are partial diagrammatic views of the applicator device shown in FIGS. 4 and 5, illustrating various exemplary embodiments of an applicator element.
Figure 7:
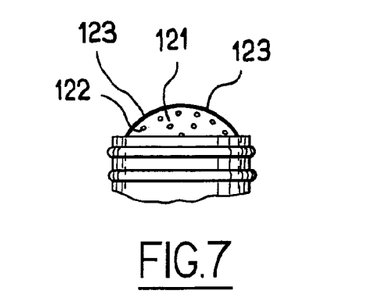

In some exemplary embodiments, the applicator element may comprise a material adapted to retain the substance P by capillarity. For example, the application element may comprise a tuft of bristles 120, as shown in FIG. 6, and/or a piece of elastomer 121 (e.g., silicon), as shown in FIG. 7. The applicator element may comprise at least one orifice 122 that may open out into its outside surface to feed the surface with the substance P.

In an exemplary embodiment, the electrodes 123 may also be present on its outside surface, where appropriate.

Throughout the description, including in the claims, the term "a" should be understood as referring to both the singular and the plural unless otherwise specified to the contrary.

It will be apparent to those skilled in the art that various modifications and variations can be made to the structure and methodology of the present invention. Thus, it should be understood that the invention is not limited to the examples discussed in the specification. Rather, the present invention is intended to cover modifications and variations.

What is claimed is:

1. A device for applying a substance, the device comprising:
   a substance;
   an applicator element comprising a surface, the applicator element being configured to be loaded with the substance; and
   an electrical exciter comprising at least two electrodes permanently in contact with the applicator element and enabling electrical current to flow to the applicator element via said electrodes,
   wherein the surface of the applicator element is configured to apply the substance to skin or keratinous fibers, and
   wherein the substance comprises at least one of a skin care product and a cosmetic product.

2. A device according to claim 1, wherein the applicator element is electrically conductive when dry.

3. A device according to claim 2, wherein the applicator element comprises a material that is intrinsically generally non-conductive, the material containing a filler that is electrically conductive.

4. A device according to claim 3, wherein the material comprises a plastic material.

5. A device according to claim 3, wherein the filler comprises electrically conductive particles.

6. A device according to claim 5, wherein the filler comprises at least one of metal particles and graphite particles.

7. A device according to claim 6, wherein the metal particles comprise at least one of copper, aluminum, and silver.

8. A device according to claim 1, wherein the applicator element is electrically insulative when dry.

9. A device according to claim 1, wherein the applicator element is porous.

10. A device according to claim 1, wherein the applicator element is elastically deformable.

11. A device according to claim 1, wherein the applicator element comprises at least one of a foam, a sintered element, a felt, a tuft of bristles, and a piece of elastomer.

12. A device according to claim 11, wherein the applicator element comprises the piece of elastomer and the piece of elastomer comprises silicone.

13. A device according to claim 1, wherein the applicator element comprises a material that is adapted to retain the substance by capillarity.

14. A device according to claim 1, wherein the applicator element is hydrophilic.

15. A device according to claim 1, wherein at least one of the electrodes is embedded at least partially in the applicator element.

16. A device according to claim 1, wherein at least one of the electrodes lacks any contact with a surface of the applicator element that is configured to contact a zone to which the substance is to be applied.

17. A device according to claim 1, further comprising a handle, wherein at least one of the electrodes is fixedly fastened to the handle.

18. A device according to claim 1, further comprising a compartment for receiving an electrical power supply.

19. A device according to claim 18, wherein the electrical power supply comprises at least one of a capacitor and an optionally-rechargeable electric battery.

20. A device according to claim 1, wherein the electrical exciter comprises a connector for connecting the electrical exciter to an electrical adapter that is connected to mains.

21. A device according to claim 1, wherein a voltage across terminals of the electrodes is less than about 30 V.

22. A device according to claim 21, wherein the voltage across the terminals of the electrodes ranges from about 1 V to about 9 V.

23. A device according to claim 1, wherein the electrical exciter comprises a power adjusting member for adjusting electrical power supplied to the electrodes.

24. A device according to claim 1, wherein the electrical exciter comprises an indicator light configured to indicate whether electrical current is flowing through the electrodes.

25. A device according to claim 1, further comprising a reservoir containing the substance, the reservoir being arranged to reload the applicator element with the substance.

26. A device according to claim 25, wherein the substance is electrically conductive.

27. A device according to claim 1, wherein the substance comprises a hair care product.

28. A device according to claim 1, further comprising:
a receptacle comprising a reservoir containing the substance; and
an applicator comprising a handle secured to the applicator element,
wherein the applicator is configured to be removably placed on the receptacle so as to enable loading the applicator element with the substance.

29. A device according to claim 28, wherein the handle comprises a compartment for accommodating an electrical power supply.

30. A device according to claim 29, wherein, when the applicator element is received in the housing of the receptacle for storage purposes, the applicator element is compressed.

31. A device according to claim 28, wherein the receptacle comprises a housing for receiving the applicator element when the applicator is removably placed on the receptacle.

32. A device according to claim 31, wherein the housing comprises an end wall arranged to restrict passage of the substance from the reservoir towards the applicator element.

33. A device according to claim 32, wherein the end wall comprises one or more orifices.

34. A device according to claim 1, further comprising a receptacle containing the substance to be applied, wherein the applicator element is permanently fastened to the receptacle.

35. A device according to claim 34, wherein the receptacle comprises a compartment for accommodating an electrical power supply.

36. A device according to claim 35, further comprising a case configured to accommodate an electrical power supply and to releasably receive at least part of said receptacle, the case comprising first electrical contacts arranged to co-operate with second electrical contacts secured to the receptacle for supplying electrical current to the electrodes.

37. A device according to claim 1, further comprising a switch for controlling supply of electrical power to the electrodes.

38. A device according to claim 1, further comprising a handle with a compartment for accommodating an electrical power supply, wherein the compartment is provided with a resilient return member arranged to urge the electrical power supply away from a first position, in which the electrical power supply electrically connects to the electrodes, towards a second position, in which the electrical power supply is disconnected from the electrodes.

39. A device according to claim 38, wherein the resilient return member comprises a spring.

40. A device for applying a substance, the device comprising:
a substance;
a handle;
an applicator element secured to the handle and comprising a surface, the applicator element being configured to be loaded with substance; and
an electrical exciter comprising at least two electrodes permanently in contact with the applicator element and enabling electrical current to flow to the applicator element via said electrodes, wherein the device lacks any reservoir of substance associated with the applicator element for feeding the applicator element with substance,
wherein the substance is configured to be applied to skin or keratinous fibers.

41. A device according to claim 40, further comprising a compartment for accommodating an electrical power supply.

42. A method of performing cosmetic treatment, the method comprising:
providing the device of claim 1;
loading the applicator element with the substance; and
applying the substance, via the applicator element, to a zone to be treated.

43. A method according to claim 42, further comprising:
causing electrical current to flow through the electrodes while simultaneously applying the substance to the zone for treatment.

44. A method according to claim 42, wherein the substance is applied using the applicator element without causing electrical current to flow through the electrodes.

45. A method according to claim 44, further comprising:
causing electrical current to flow through the electrodes substantially without applying any additional quantity of substance, the applicator element being in contact with a zone that has already been covered with the substance.

46. A method according to claim 42, wherein the applicator element is electrically insulative when dry, wherein the loading comprises loading the applicator element with a substance that is electrically conductive, and wherein the method further comprises causing electrical current to flow through the electrodes.

* * * * *